US010661097B2

(12) United States Patent
Tallinen et al.

(10) Patent No.: US 10,661,097 B2
(45) Date of Patent: May 26, 2020

(54) VMAT TREATMENT PLANNING USING MULTICRITERIA OPTIMIZATION AND A PROGRESSIVE OPTIMIZATION SCHEME

(71) Applicants: Varian Medical Systems International AG, Cham (CH); Varian Medical Systems, Inc., Palo Alto, CA (US)

(72) Inventors: Tuomas Tallinen, Espoo (FI); Stephen K. Thompson, Pacific Grove, CA (US); Joona Hartman, Espoo (FI); Perttu Niemelä, Espoo (FI)

(73) Assignees: Varian Medical Systems, Inc., Palo Alto, CA (US); Varian Medical Systems International AG, Cham (CH)

( * ) Notice: Subject to any disclaimer, the term of this patent is extended or adjusted under 35 U.S.C. 154(b) by 281 days.

(21) Appl. No.: 15/711,516

(22) Filed: Sep. 21, 2017

(65) Prior Publication Data

US 2019/0083814 A1 Mar. 21, 2019

(51) Int. Cl.
*A61N 5/00* (2006.01)
*A61N 5/10* (2006.01)

(52) U.S. Cl.
CPC ......... *A61N 5/1031* (2013.01); *A61N 5/1045* (2013.01); *A61N 5/1047* (2013.01); *A61N 5/1049* (2013.01); *A61N 2005/1074* (2013.01); *A61N 2005/1087* (2013.01)

(58) Field of Classification Search
CPC .... A61N 5/103; A61N 5/1031; A61N 5/1041; A61N 5/1047; A61N 5/1081
USPC ........................................................ 600/1–8
See application file for complete search history.

(56) References Cited

U.S. PATENT DOCUMENTS

2012/0045035 A1 2/2012 Nord et al.
2018/0021594 A1* 1/2018 Papp ..................... A61N 5/103
600/1

FOREIGN PATENT DOCUMENTS

WO 2011153639 12/2011

OTHER PUBLICATIONS

Chen et al., "Multi Criteria Optimization Informed VMAT Planning", Medical dosimetry, vol. 39, No. 1, 2014, 20 pages.
Monz et al., "Pareto Navigation—Algorithmic Foundation of Interactive Multi-Criteria IMRT Planning", Physics in Medicine and Biology, vol. 53, No. 4, Feb. 21, 2008, pp. 985-998.
European International No. EP18194766.4, "Extended European Search Report", dated Feb. 18, 2019, 6 pages.
European Patent Application No. EP18194766.4, "Office Action", dated Feb. 19, 2020, 4 pages.

* cited by examiner

*Primary Examiner* — John P Lacyk
(74) *Attorney, Agent, or Firm* — Kilpatrick Townsend & Stockton LLP

(57) ABSTRACT

Computer-implemented methods and systems can be used to facilitate generation of VMAT treatment plans for providing radiation therapy to patients. Starting from a seed plan, a library of alternative plans, each with an associated outcome for a set of treatment objectives, can be generated via a set of parallel optimization operations performed on the seed plan. A graphical user interface is provided, via which the user can navigate within a treatment space defined by the alternative plans to identify a satisfactory outcome. Based on the satisfactory outcome and a candidate plan selected from the alternative plans, a deliverable VMAT treatment plan can be generated using another optimization operation.

28 Claims, 12 Drawing Sheets

Direction of leaf movement

US 10,661,097 B2

VMAT TREATMENT PLANNING USING MULTICRITERIA OPTIMIZATION AND A PROGRESSIVE OPTIMIZATION SCHEME

BACKGROUND

The present disclosure relates generally to treatment planning for radiation therapy and more particularly to treatment planning systems and methods that use multicriteria optimization and a progressive optimization scheme to develop treatment plans for volumetric modulated arc therapy (VMAT).

In general, radiation therapy consists of the use of ionizing radiation to treat living tissue, usually tumors. Many different types of ionizing radiation are used in radiation therapy, including high-energy x-rays, electron beams, and proton beams. The process of administering radiation therapy to a patient can be similar across different types of radiation. Typically, an external-beam radiation treatment system is used. Such systems provide a linear accelerator that produces a beam of the desired type at a beam source and collimators including a multileaf collimator (MLC) to shape the beam that emerges from the beam source. The beam delivery system (including the beam source and collimators) is generally mounted on a movable gantry that can be moved around a treatment couch on which a patient is placed, allowing the radiation beam to be delivered from different angles relative to the patient.

Systems of this kind are used for various treatment options. One option is intensity-modulated radiotherapy (IMRT), in which the beam source is positioned at a desired angle, and the MLC is modulated to control the dose received by different tissues. During a treatment session, the beam source and/or the MLC may be repositioned, allowing radiation to be delivered from different angles. In IMRT, the beam source remains stationary while radiation is being delivered. Another treatment option is volumetric modulated arc therapy (VMAT), in which the beam source traverses an arc around the patient while delivering radiation. In both IMRT and VMAT, the overarching goal is to deliver a therapeutically effective dose of radiation (typically a high and uniform dose) to a target volume (typically a tumor) within the patient's body while minimizing the dose delivered to surrounding tissues (in particular, healthy organs that may be located close to the target volume).

Effective radiation therapy requires treatment planning to determine machine parameters that will optimally achieve the overarching goal. In the case of IMRT, a treatment plan may specify machine parameters such as positions of the beam source and collimators (including MLC leaf settings), beam intensity (e.g., dose rate), and duration of exposure (also referred to as "beam-on time"); the plan may include multiple control points, each defined by a set of machine parameters. In the case of VMAT, a treatment plan may specify all of the same machine parameters as in IMRT, plus additional parameters defining an arc to be traversed and in some instances speed of traversing the arc. During treatment, a treatment plan can be used to control operation of the radiotherapy system, and operating the radiotherapy system according to the treatment plan results in delivering a desired dose distribution to the patient.

Treatment planning is usually approached via the "inverse" problem of determining the optimal combination of machine parameters—such as beam intensity, beam shaping, beam direction(s), exposure duration—to deliver a desired total radiation dose to the target volume (or multiple target volumes) while minimizing the dose delivered to nearby organs (sometimes referred to as "organs at risk," or "OAR"). Given the many degrees of freedom, the inverse problem is generally not amenable to an analytic solution.

In the case of IMRT, interactive tools have been developed to facilitate finding a solution to the inverse problem. Traditionally, such tools are designed to find a single optimal solution by minimizing the value of an objective function. To formulate an objective function for an IMRT optimization problem, a desired outcome is first defined as a vector in a multidimensional space. A set of alternative solutions (which may be an infinite set) is defined, where each alternative solution has an associated alternative outcome, also defined as a vector in the multidimensional space. A cost function is defined to quantify a distance (in the multidimensional space) between any given alternative outcome and the desired outcome. Euclidean or other distance metrics can be used, and different components of the outcome vector may be assigned different weights in the cost function. The optimum solution can be identified by finding the alternative solution that minimizes the cost function.

For purposes of applying cost-function-based optimization processes to radiation therapy treatment planning, the outcome vector may be defined as a dose distribution that includes doses for at least one target volume and some number of non-target volumes for which low dose is optimal and no dose is ideal but generally not achievable. It is not immediately apparent how the different objectives should be weighted, and accordingly it may be desirable to allow the user to explore the effects of different weightings, a procedure sometimes referred to as multicriteria optimization.

Interactive tools exist to facilitate such exploration in the context of IMRT. Such tools receive a set of treatment objectives (e.g., identifying some number of volumes of interest and a desired dose for each such volume). Based on the treatment objectives, a library (e.g., database) of alternative plans is generated, e.g., by creating a Pareto-optimal IMRT plan for each treatment objective in turn, with each alternative plan having an associated dose matrix indicating the dose in each volume specified in the treatment objectives. The user (e.g., a radiation oncologist or other medical professional) interacts with the library through a graphical user interface to explore a navigation space defined by the alternative plans. Visualization tools allow the user to define an interpolation among the plans in the library; for instance, the user can operate control elements (e.g., onscreen sliders) to adjust the interpolation parameters and observe the effect on dose distribution. Once the user has achieved a desired dose distribution by adjusting the interpolation parameters, a final treatment plan is generated by an interpolation of database plans using the user-adjusted parameters. Such interfaces can provide a real-time, intuitive technique to facilitate treatment planning for IMRT.

SUMMARY

Previously, it has not been possible to adapt these interactive techniques to VMAT treatment planning based on utilization of direct machine parameters. Generating a representative set of alternative VMAT plans is considerably slower than for IMRT plans, in part because of the extra degrees of freedom introduced by allowing the beam to move during exposure. In addition, interpolating between VMAT treatment plans to generate a final plan is ineffective, due to the non-convex nature of machine parameter limits related to VMAT delivery.

Certain embodiments of the present invention overcome such problems, allowing for interactive VMAT treatment planning systems and methods. The initial task of generating alternative plans defining a navigation space is simplified by starting from a "seed" plan, which may be a VMAT plan created by a user that balances different treatment objectives (e.g., doses delivered to specific target and non-target volumes) but may be less than clinically optimal. Starting from the seed plan, a library of alternative plans can be generated by adjusting machine parameters of the seed plan to optimize each treatment objective in turn. Each alternative plan can have an associated outcome (e.g., dose distribution matrix), which can be determined using simulation techniques and/or clinical data. The navigation space defined by the alternative plans can be used to support a graphical user interface (GUI) that allows the user to view hypothetical treatment outcomes (e.g., dose distributions) generated by interpolating treatment outcomes associated with some or all of the alternative plans. The user can dynamically adjust the interpolation weights by operating controls (e.g., a set of sliders) to modify the relative importance of various treatment objectives and can view the effect on outcome in real time. Once the user has identified a satisfactory treatment outcome by operating the controls, a deliverable treatment plan can be determined by identifying a candidate plan in the space of alternative plans and using the (user-specified) satisfactory treatment outcome to perform an optimization operation on the candidate plan to generate a deliverable plan. The candidate plan can be, for example, the alternative plan whose treatment outcome is closest to the (user-specified) satisfactory treatment outcome (as determined using a cost function with weights defined based on the control settings), and the deliverable plan can be generated by performing a machine parameter adjustment on the candidate plan (e.g., by continuing its optimization with modified objectives) to minimize the difference between plan outcome and the (user-specified) satisfactory treatment outcome. In some embodiments, the deliverable plan thus generated can be used as a new seed plan for a next stage of optimization, allowing for an iterative optimization process. At each stage, the user may decide whether to use the deliverable plan in a VMAT treatment or proceed with another iteration.

The following detailed description will provide a better understanding of the nature and advantages of the claimed invention.

DEFINITIONS

Figure 1:
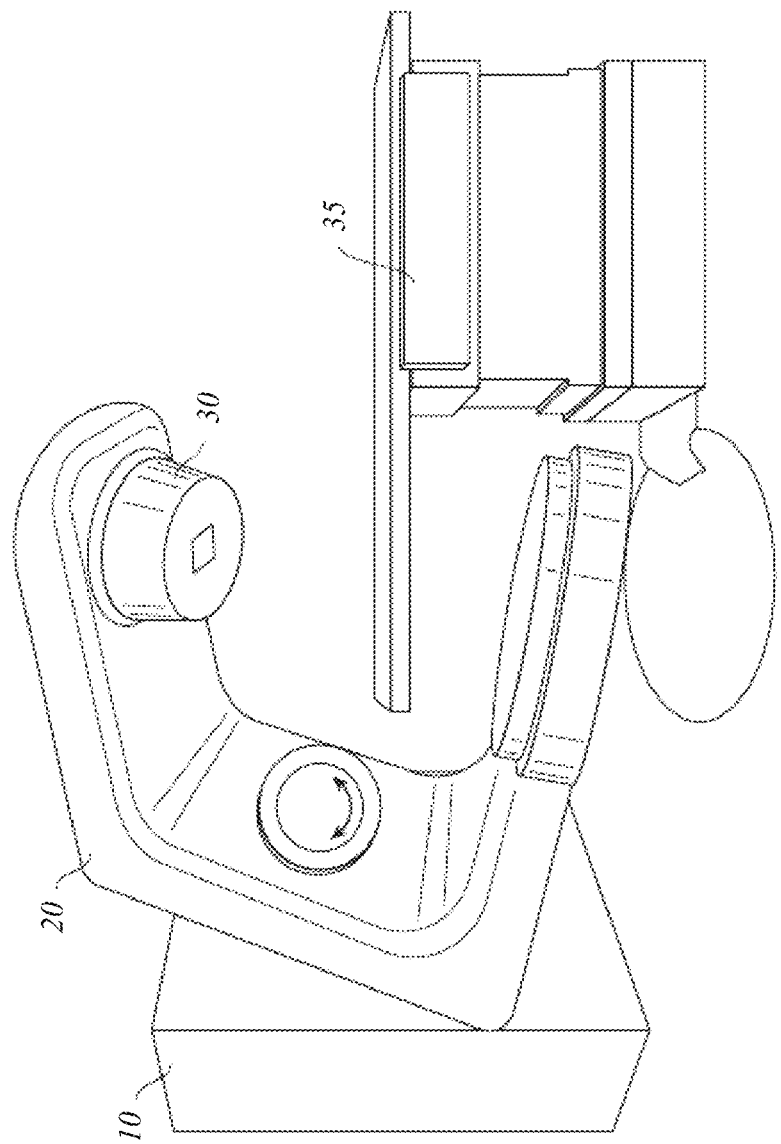
FIG. 1 shows a perspective view of a radiation treatment system that may be used in connection with the present invention.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" refer to tissue intended to receive a therapeutic prescribed dose. The irradiated volume is generally larger than the target volume and may include organs or tissues that are not intended to receive a therapeutic dose. Such organs or tissues are sometimes referred to as "organs at risk" (OAR).

A "radiation treatment plan" (also referred to as a "treatment plan" or "plan") can include a dose distribution, machine parameters for achieving the dose distribution for a given patient, and information about the given patient. A "dose distribution" provides information about the variation in the dose of radiation with position. A dose distribution can be represented in many formats, e.g., a dose volume histogram (DVH) or a dose matrix. A DVH can summarize three-dimensional (3D) dose distributions in a graphical format, e.g., where the horizontal axis is the dose (e.g., in units of grays (Gy)) absorbed by a particular volume or structure (which can be the target volume, an OAR, or any other well-defined volume) and the vertical axis is a volumetric percentage. In a differential DVH, the height of a bar at a particular dose indicates the volumetric percentage of the volume in question that receives the particular dose. In a cumulative DVH, the height of a bar at a particular dose represents the volumetric percentage of the volume in question that receives greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can show the dose that each part of the body receives.

A "dose prediction model" receives patient data and machine parameters and outputs a dose distribution that is predicted to be obtained. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test radiation treatment plans whose dose distribution has been determined via other means (e.g., by optimizing a cost function). For example, the accuracy can be determined based on how well the model predicts the actual dose distributions obtained by optimizing a cost function.

"Monitor unit" (MU) is a measure of machine output from a clinical accelerator for radiation therapy such as a linear accelerator. Monitor units are measured by monitor chambers, which are ionization chambers that measure the dose delivered by a beam and built into the treatment head of radiotherapy linear accelerators. Linear accelerators are calibrated to give a particular absorbed dose under particular conditions, although the definition and measurement configuration will vary between centers.

Two common definitions of monitor units are: (1) the monitor chamber reads 100 MU when an absorbed dose of 1 gray (100 rads) is delivered to a point at the depth of maximum dose in a water-equivalent phantom whose surface is at the isocenter of the machine (i.e. usually at 100 cm from the source) with a field size at the surface of 10 cm×10 cm; and (2) the monitor chamber reads 100 MU when an absorbed dose of 1 Gy (100 rad) is delivered to a point at a given depth in the phantom with the surface of the phantom positioned so that the specified point is at the isocenter of the machine and the field size is 10 cm×10 cm at the isocenter.

Some linear accelerators are calibrated using source-to-axis distance (SAD) instead of source-to-surface distance (SSD), and calibration (monitor unit definition) may vary depending on hospital custom. Early radiotherapy was performed using "constant SSD" treatments, and so the definition of monitor unit was adopted to reflect this calibration geometry. Modern radiotherapy is performed using isocentric radiation treatment plans, so newer definitions of the monitor unit are based on geometry at the isocenter based on the source-to-axis distance (SAD).

The term "spatial point" used in this disclosure in relation to a treatment field refers to a geometrical point associated with a set of values for treatment axes coordinates of an external-beam radiation treatment system. A spatial point is defined by the position of the isocenter, the position and angles of the patient support, the gantry angle, the collimator angle, and the position of each MLC leaf. The term "control point" refers to a parametrical point of a radiation treatment field that includes spatial information about the treatment axes and may also specify collimator settings, beam intensity or dose rate (e.g., using MU count and/or the related concept of the meterset weight), and/or speed of motion of the beam source (including a speed of a movable gantry supporting the beam source).

DETAILED DESCRIPTION

Certain embodiments of the present invention relate to interactive VMAT treatment planning systems and methods. The initial task of generating alternative plans defining a navigation space is simplified by starting from a "seed" plan, which may be a VMAT plan created by a user that balances different treatment objectives (e.g., doses delivered to specific target and non-target volumes) but may be less than clinically optimal. Starting from the seed plan, a library of alternative plans can be generated by adjusting machine parameters of the seed plan to optimize each alternative plan in turn. Each alternative plan can have an associated outcome (e.g., an associated dose distribution matrix), which can be determined using simulation techniques and/or clinical data. The navigation space defined by the alternative plans can be used to support a graphical user interface (GUI) that allows the user to view hypothetical treatment outcomes (e.g., dose distributions) generated by interpolating treatment outcomes associated with some or all of the alternative plans. The user can dynamically adjust the interpolation weights by operating controls (e.g., a set of sliders) to modify the relative importance of various treatment objectives and can view the effect on outcome in real time. Once the user has identified a satisfactory treatment outcome by operating the controls, a deliverable treatment plan can be determined by identifying a candidate plan in the space of alternative plans and using the (user-specified) satisfactory treatment outcome to perform an optimization operation on the candidate plan to generate a deliverable plan. The candidate plan can be, for example, the alternative plan whose treatment outcome is closest to the (user-specified) satisfactory treatment outcome (as determined using a cost function with weights defined based on the control settings), and the deliverable plan can be generated by performing a machine parameter adjustment on the candidate plan (e.g., by continuing its optimization with modified objectives) to minimize the difference between plan outcome and the (user-specified) satisfactory treatment outcome. In some embodiments, the deliverable plan thus generated can be used as a new seed plan for a next stage of optimization, allowing for an iterative optimization process. At each stage, the user may decide whether to use the deliverable plan in a VMAT treatment or proceed with another iteration.

External beam therapy (EBT), also called external radiation therapy, is a method for delivering a beam or several beams of high-energy x-rays to a patient's tumor. Beams are generated outside the patient (usually by a linear accelerator) and are targeted at the tumor site.

Figure 2:
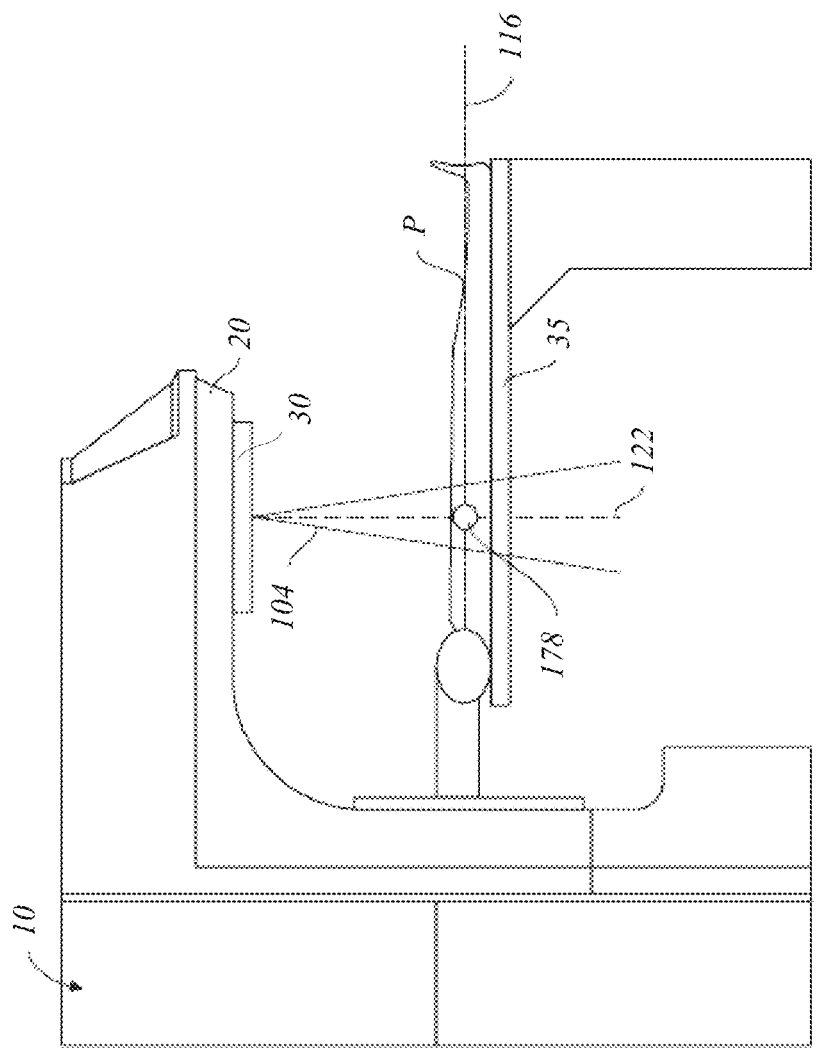
FIG. 2 shows a side view of the radiation treatment system of FIG. 1.

FIGS. 1 and 2 depict a radiation treatment system 100 that may be used in connection with the present invention. FIG. 1 shows a perspective view of radiation treatment system 100 (in this case incorporating a linear accelerator). Radiation treatment system 100 may be capable of generating either an electron (particle) beam or an x-ray (photon) beam for use in the radiotherapy treatment of a patient on a treatment couch 35. For purposes of the present description, x-ray irradiation will be assumed. However, it will be appreciated by those skilled in the art that the same principles apply to other systems, including electron beam systems and heavy-ion (e.g., proton) beam systems.

Stand 10 supports a rotatable gantry 20 with a treatment head 30. Next to stand 10 there is arranged a control unit (not shown) which includes control circuitry for controlling the different modes of operation of radiation treatment system 100. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

FIG. 2 shows a somewhat more detailed side view of radiation treatment system 100. A patient P is shown lying on treatment couch 35. X-rays formed as described above are emitted from the metal target in treatment head 30 in a divergent beam 104. Typically, a patient plane 116, which is perpendicular to the page in FIG. 2, is positioned about one meter from the x-ray source (e.g., the metal target), and the axis of gantry 20 is located in patient plane 116, such that the distance between the target in treatment head 30 and isocenter 178 remains constant when gantry 20 is rotated. Isocenter 178 is a point located at the intersection between patient plane 116 and the central axis of beam 122. A treatment volume to be irradiated is located about isocenter 178.

Figure 3:
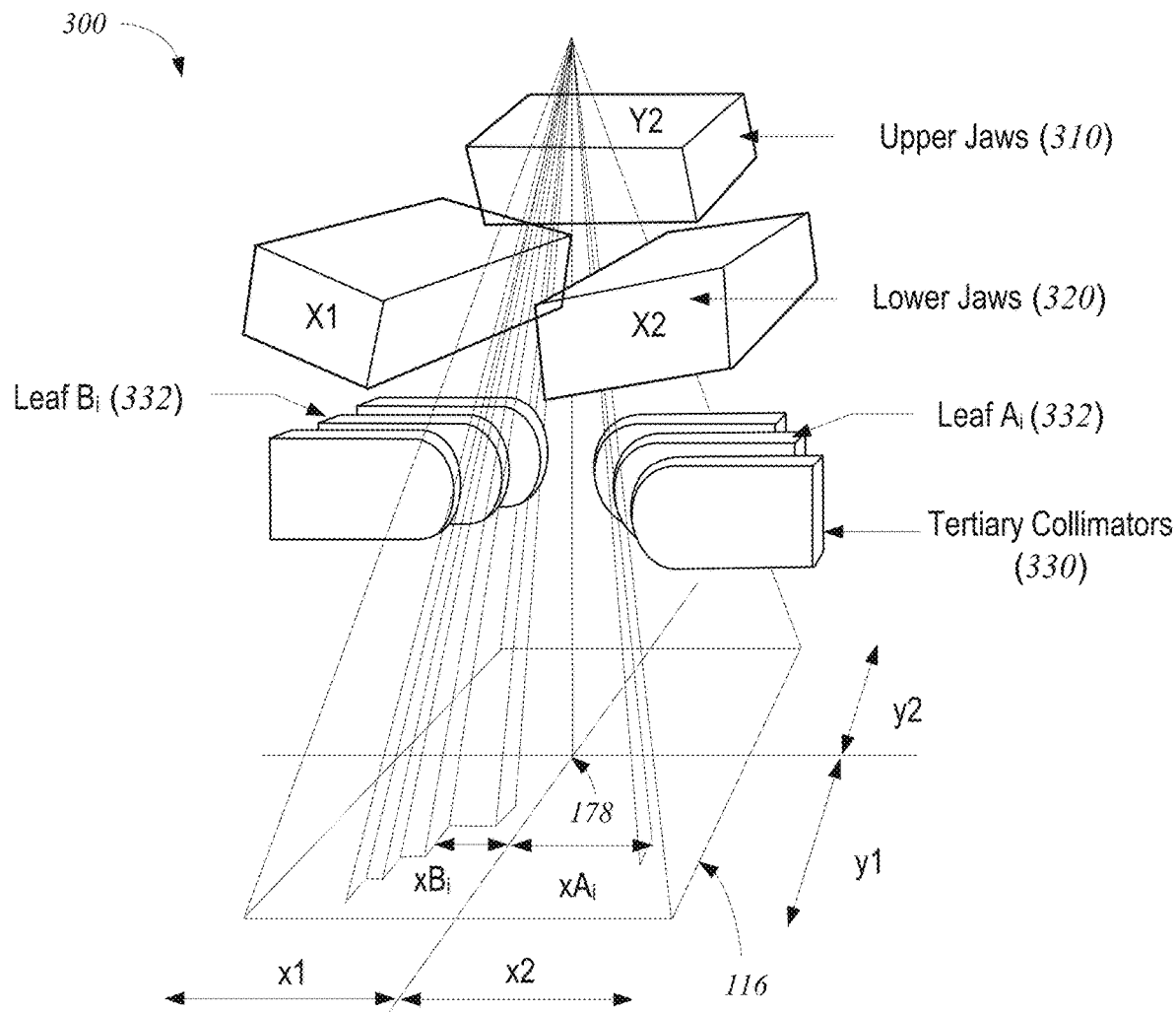
FIG. 3 shows schematically a photon collimation system that may be included in the radiation treatment system of FIG. 1.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multileaf collimator (MLC) 330. The field dimensions in patient plane 116 and the location of isocenter 178 are indicated. Upper jaws 310, lower jaws 320, and leaves 332 of MLC 330 are made at least partially of an x-ray blocking material and are positioned in treatment head 30 (shown in FIG. 2) to define the width of the x-ray beam at patient plane 116. Typically, jaws 310 and 320 are moveable and, when fully open, define a maximum beam width of about 40 cm×40 cm at patient plane 116. MLC 330 is positioned at the exit of treatment head 30, to further shape the x-ray beam. Since its introduction in 1990 the MLC has become a standard feature of most radiation treatment systems. Current MLCs sold by the assignee of the present invention use up to 120 individually controllable leaves, typically thin slices of tungsten, that can be moved into or out of the x-ray beam under the control of system software.

Figure 4:
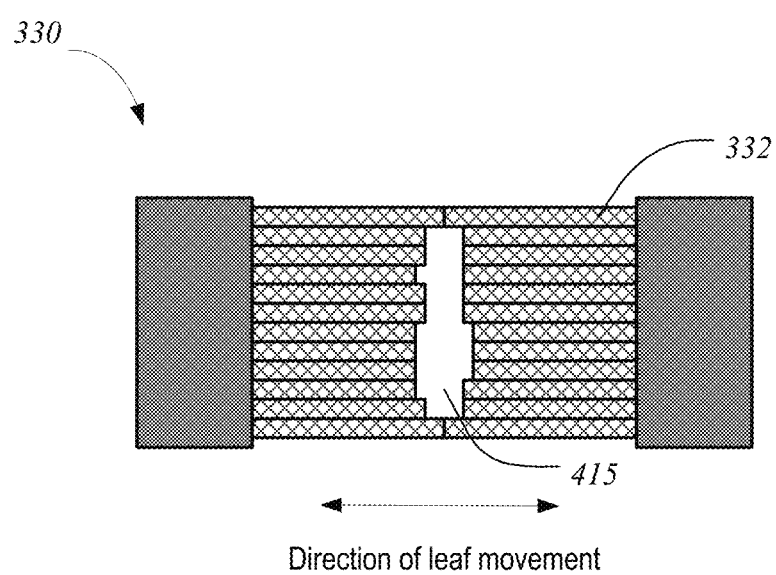
FIG. 4 shows an exemplary multileaf collimator plane that may be used in the photon collimation system of FIG. 3.

FIG. 4 shows an exemplary MLC plane having a plurality of leaves 332, arranged in opposing pairs, and an aperture 415 created by selected leaf movements. Radiation passes through and is shaped by aperture 415. Thus, MLC 330 can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to isocenter 178 in the treatment path of the x-ray beam, is defined by jaws 310 and 320, the leaf sequence of MLC 330, and the collimator angle, i.e., the angle at which MLC 330 sits in treatment head 30. In some embodiments, the position of jaws 310 and 320, the leaf sequence of MLC 330, and the collimator angle are all controllable machine parameters; in other embodiments, some of these parameters may be fixed.

Figure 5:
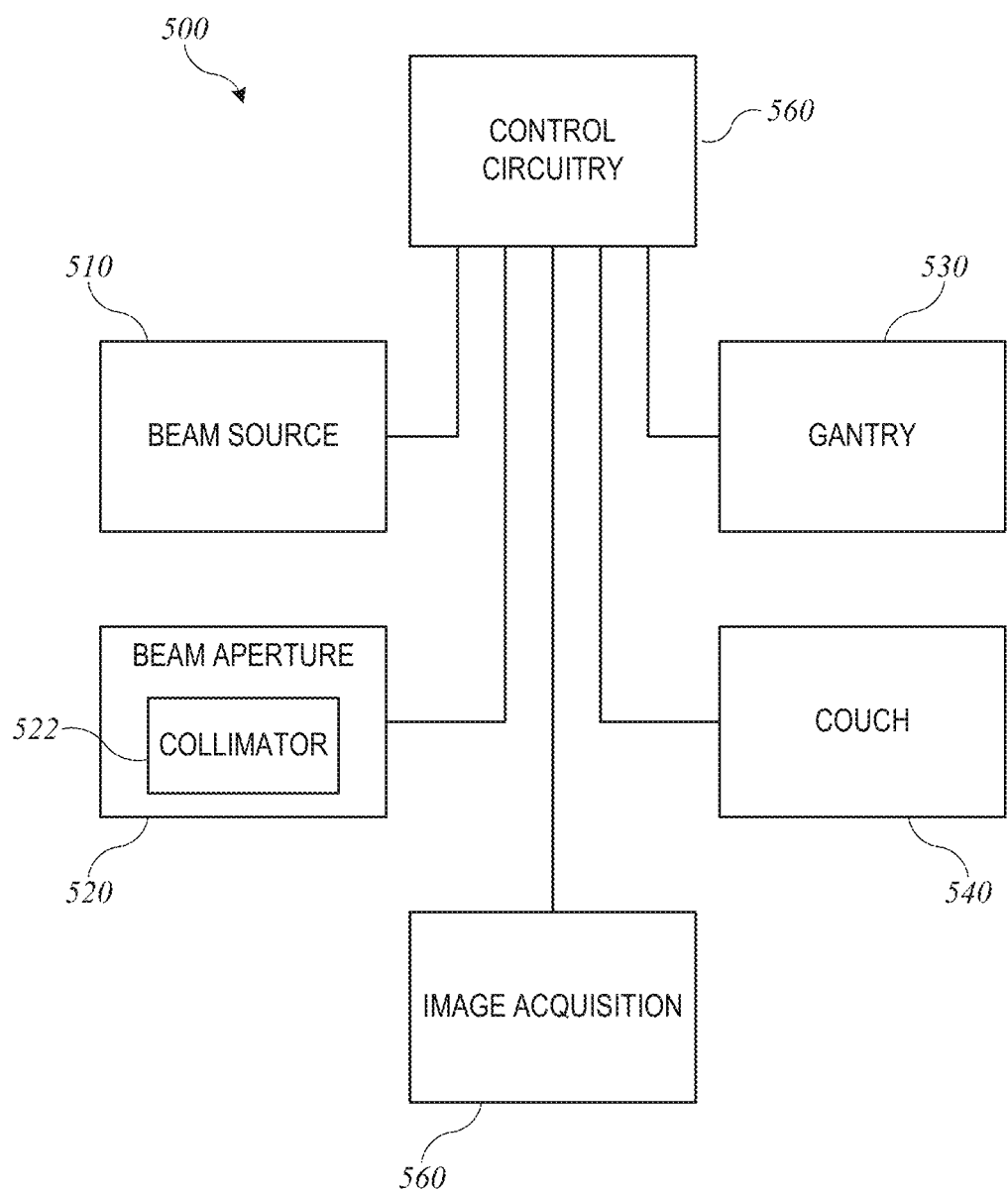
FIG. 5 shows a block diagram of an external-beam radiation treatment system that may be used in connection with the present invention.

FIG. 5 shows a block diagram of an external-beam radiation treatment system 500 implementing radiation treatment system 100 of FIGS. 1 and 2. Radiation treatment system 500 includes a beam source 510, a beam aperture 520, a gantry 530, and a couch 540. Beam source 510 is configured to generate a beam of therapeutic radiation. This beam of radiation may include x-rays, particles, or the like. Beam aperture 520 includes an adjustable multi-leaf collimator (MLC) 522, which can be an implementation of MLC 330 described above, for spatially filtering the radiation beam. Couch 540, which can be an implementation of treatment couch 35 of FIGS. 1 and 2, is configured to support and position a patient during treatment. Couch 540 may have six degrees of freedom (the translational offsets X, Y, and Z, and the rotation, pitch, and yaw), which may be treated as machine parameters.

Gantry 530, which can be an implementation of gantry 20, houses beam source 510 and beam aperture 520. Gantry 530 can be movable, e.g., rotatable, around a fixed axis, and volumetric modulated arc therapy (VMAT) treatment can be performed by rotating gantry 530 while beam source 510 is delivering beam. The arc to be traversed (e.g., starting and ending points) and/or speed of traversal can be treated as additional machine parameters.

In some embodiments, beam source 510 can be configured to generate imaging radiation as well as therapeutic radiation. Accordingly, radiation treatment system 500 may also include an image acquisition system 550 that comprises one or more imaging detectors mounted to gantry 530 (e.g., on an arm opposite beam aperture 520).

Radiation treatment system 500 further includes control circuitry 560 for controlling the operation of beam source 510, beam aperture 520, gantry 530, couch 540, and image acquisition system 550. Control circuitry 560 may include hardware, software, and memory for controlling the operation of these various components of radiation treatment system 500. Control circuitry 560 can comprise a fixed-purpose hard-wired platform or can comprise a partially or wholly-programmable platform. Control circuitry 560 can be configured to carry out various steps, actions, and other functions described herein. In some embodiments, control circuitry 560 may include a memory for receiving and storing a radiation treatment plan that defines the spatial points or control points of one or more treatment fields. Control circuitry 560 may then send control signals to the various components of radiation treatment system 500, such as beam source 510, beam aperture 520, gantry 530, and couch 540, to execute the radiation treatment plan. In some embodiments, control circuitry 560 may include an optimization engine to determine a radiation treatment plan; in other embodiments, an optimization engine can be provided in a separate computer system that delivers a radiation treatment plan to control circuitry 560 via a network interface or computer-readable storage medium.

Figure 6:
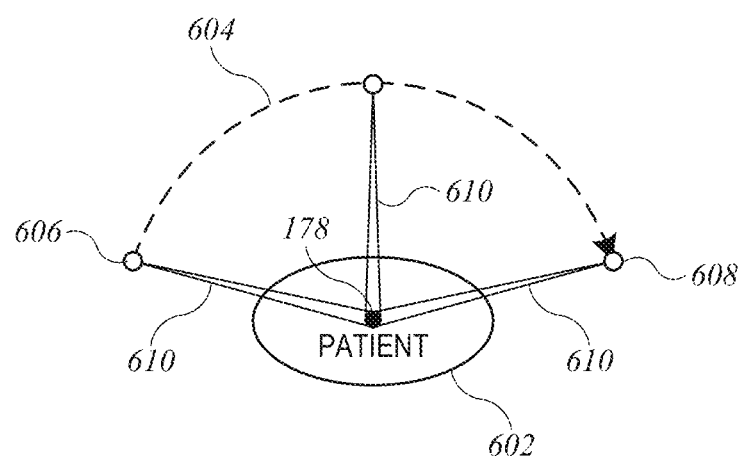
FIG. 6 shows a simplified schematic representation of a VMAT treatment plan that can be generated according to an embodiment of the present invention.

In certain embodiments of the present invention, radiation treatment plans that can be executed by radiation treatment system 100 (or radiation treatment system 500) include VMAT treatment plans. FIG. 6 shows a simplified schematic representation of a VMAT treatment plan that can be generated according to an embodiment of the present invention. Patient 602 is assumed to be positioned on treatment couch 35. Isocenter 178 is indicated as a black dot, and patient can be positioned such that isocenter 178 is within the target volume (e.g., a tumor to be irradiated). A VMAT arc 604 can be defined by rotation of gantry 20 about its axis. More specifically, gantry 20 rotates from a starting orientation at which treatment head is located at starting position 606 to an ending orientation at which treatment head is located at ending position 608. During treatment, beam 610 is continuously emitted from treatment head 30 while treatment head 30 traverses VMAT arc 604 from starting position 606 to ending position 608. During traversal of VMAT arc 604, the beam size (e.g., defined by the jaws and MLC as shown in FIG. 3) and the position of patient 602 (controlled by the degrees of freedom of treatment couch 35) may be held constant or varied. Beam angle may also be held constant relative to gantry 20 or varied.

For purposes of controlling the machine parameters, starting position 606 and ending position 608 may each be identified as a control point for a VMAT treatment plan, and a set of machine parameters defining beam aperture, dose rate, and patient settings can be associated with each control point. In some embodiments, one or more additional intermediate control points 612 may be defined along VMAT arc 604, and the VMAT treatment can be performed by making a series of smooth transitions between the control points. In addition to two or more control points, a VMAT treatment plan can include rotation speed information or other information specifying the speed of traversal of VMAT arc 604 (or a specific segment thereof). Because the direction from which beam 610 enters the body of patient 602 varies during traversal of VMAT arc 604, it is possible to provide a high dose of radiation to tissue near isocenter 178 while surrounding tissue receives a lower dose. However, optimizing the dose distribution can be a challenging problem, since VMAT treatment plans offer many degrees of freedom (i.e., separately adjustable machine parameters), and the effect of a modification may not be apparent.

Accordingly, certain embodiments of the present invention provide tools (e.g., computer-implemented methods) to facilitate optimization of VMAT treatment plans using an interactive user interface. The tools can leverage existing optimization algorithms to generate a library of alternative plans that optimize different treatment objectives, with each alternative plan having an associated outcome (e.g., dose distribution matrix). Via a graphical user interface, a user can interactively navigate the space defined by the alternative plans by adjusting the weight given to different treatment objectives, and an approximate dose distribution can be quickly computed in response to user navigation by interpolating between dose distributions associated with the various alternative plans according to the weight given to different treatment objectives. This allows the graphical user interface to provide real-time feedback responsive to adjustments made by the user. Once the user has selected a desired dose distribution, a "deliverable" treatment plan can be generated by an optimization process on a candidate plan selected from the library of alternative plans.

Figure 7:
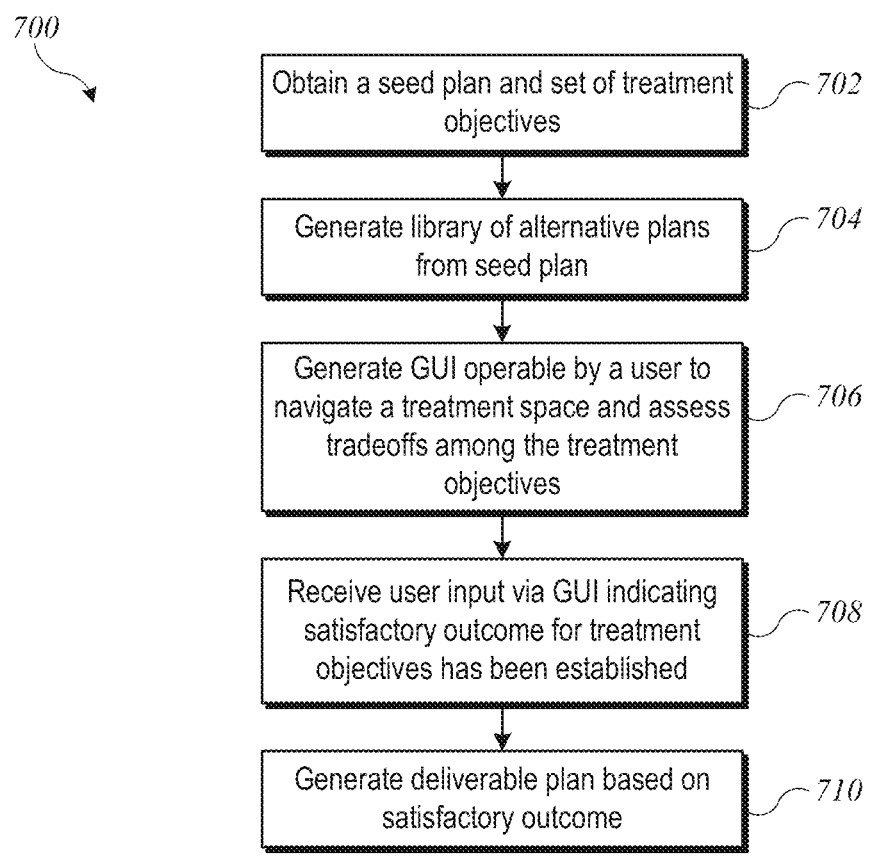
FIG. 7 shows a flow diagram of a process for optimizing a VMAT treatment plan according to an embodiment of the present invention.

FIG. 7 shows a flow diagram of a process 700 for optimizing a VMAT treatment plan according to an embodiment of the present invention. Process 700 can be performed in a computer system, e.g., using control circuitry 560 of radiation treatment system 500 (FIG. 5) or another computer system.

At block 702, process 700 can begin by obtaining a "seed" plan and a set of treatment objectives. The seed plan can be, e.g., a balanced VMAT plan created by the user using conventional tools and techniques, or it may be created in a some other manner (e.g., via a previous iteration of process 700 as described below). The treatment objectives can include identification of a set of volumes of interest and a desired radiation dose for each. For instance, one volume of interest may be a target volume (e.g., a volume occupied by a tumor), for which the treatment objective is typically to provide a therapeutically effective dose. In some cases, there may be multiple target volumes, and each can have a separate treatment objective. Other volumes of interest may correspond to different organs at risk (OARs) and/or to different portions of a single OAR, for which the treatment objective is typically to minimize the dose. In general, there are tradeoffs among these objectives, and minimizing the dose delivered to one OAR is often not possible without increasing the dose delivered to another OAR and/or reducing the dose delivered to the target volume.

At block 704, process 700 can generate a library (or set) of alternative plans from the seed plan, e.g., by modifying machine parameters of the seed plan and assessing the effect of the modification on dose distribution. For each alternative plan, the library can store machine parameters and an associated outcome (e.g., dose distribution predicted using a dose distribution model). The library can be implemented, e.g., as a database or other structured data store.

Figure 8:
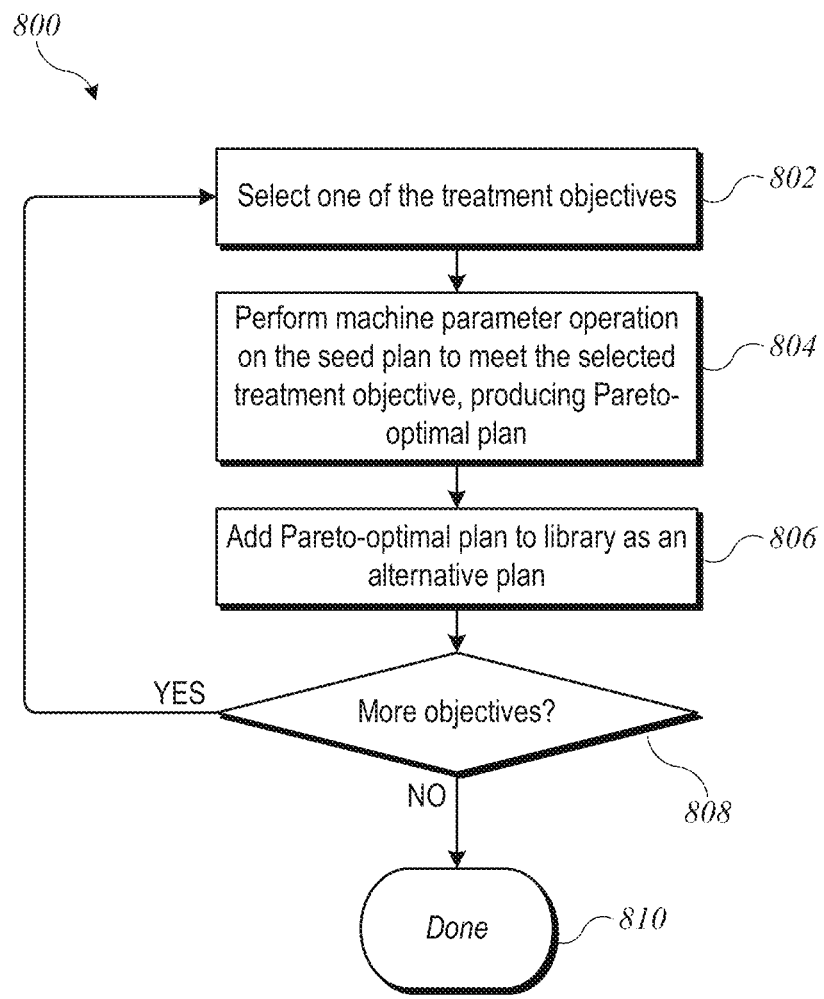
FIG. 8 shows a flow diagram of a process for generating alternative VMAT treatment plans according to an embodiment of the present invention.

In some embodiments, generation of alternative plans is based on Pareto optimization, where one treatment objective is optimized to the point where further improvement in that treatment objective worsens the outcome with respect to at least one of the other treatment objectives. FIG. 8 shows a flow diagram of a plan-generation process 800 that can be implemented at block 704 according to an embodiment of the present invention. Process 800 proceeds by adjusting machine parameters of the seed plan to generate alternative plans that are Pareto-optimal for each of the treatment objectives. At block 802, one of the treatment objectives is selected for optimization. At block 804, a machine parameter optimization is performed on the seed plan to produce a plan that is Pareto-optimal with regard to the selected treatment objective. This process can include adjusting control point weights and apertures of the seed plan and assessing the effect of the adjustment on dose distribution (e.g., using a dose distribution model). In some embodiments, the continuing optimization process may be iterative in nature to converge on an optimal plan for the selected treatment objective. At block 806, the Pareto-optimal plan produced at block 804 is added as an alternative plan to the library of alternative plans. For each alternative plan, the library can store machine parameters (e.g., the control point weights and apertures) and the calculated dose distribution. At block 808, if there are more treatment objectives to be optimized, process 800 can return to block 802 to select the next treatment objective to be optimized. Once each treatment objective has been optimized, process 800 ends at block 810, and process 700 can continue. It should be understood that, since each optimization in process 800 begins from the same seed plan, instances of process 800 can be executed in parallel for some or all treatment objectives, which can considerably speed up generation of the library of alternative treatment plans. Thus, although sequential execution is described, parallel execution is also contemplated. It should also be understood that the library is not limited to one alternative plan per treatment objective. In some embodiments, a larger number of alternative plans may be generated to better cover the space of possible tradeoffs among different treatment objectives.

Referring again to FIG. 7, after the library of alternative plans has been generated, at block 706, process 700 can generate a graphical user interface (GUI) via which the user can navigate a space defined by the set of treatment objectives to assess tradeoffs among the various treatment objectives.

Figure 9:
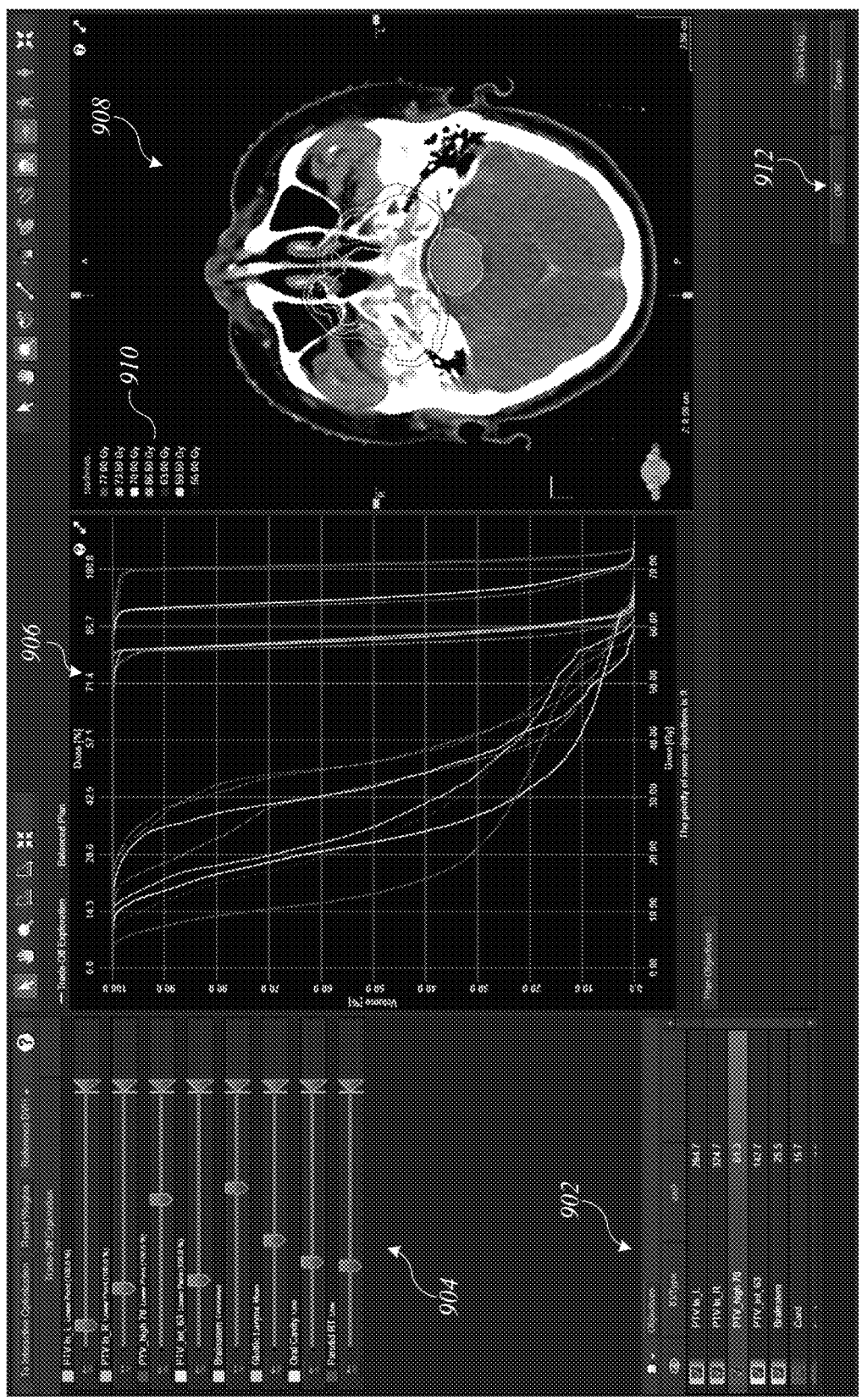
FIG. 9 shows an example of a GUI screen according to an embodiment of the present invention.

FIG. 9 shows an example of a GUI screen 900 that can be implemented according to an embodiment of the present invention. Regions 902 and 904 are control regions. In this example, region 902 provides a list of treatment objectives, e.g., a list of regions of interest selected by the user. The different treatment objectives can be color-coded to facilitate understanding of other information provided. Region 904 provides a separate user-operable control corresponding to each treatment objective. In this example, the controls are implemented as virtual sliders that the user can move (e.g., via a drag operation with a mouse, stylus, finger or other pointing device); other control types may be substituted. By moving the controls in region 904, the user can indicate relative importance (or weight) of different treatment objectives. Increasing the importance of a particular treatment objective may constrain treatment options to a particular range and may also affect the range of outcomes achievable with regard to other treatment objectives. Accordingly, when the user moves one slider, other sliders may automatically move to reflect correlations among different treatment objectives.

Regions 906 and 908 provide visual feedback regarding outcomes. In some embodiments, data displayed in regions 906 and 908 is updated automatically in real time as the user moves a slider in region 904. Shown in region 906 is a dose volume histogram (DVH) for the various regions of interest (color-coded to match regions 902 and 904). Shown in region 908 is a dose distribution map for a particular slice through the patient's body. (The color coding is indicated in legend 910.) In this example, a single sagittal slice is shown. In some embodiments, GUI screen 900 may provide additional controls to allow the user to select one or more slices to view at any given time, including transverse and/or frontal slices, as well as slices at different depths. Generation of the DVH and dose distribution map may be done by interpolating dose distributions of the alternative plans in the library, using interpolation weights generated based on the positions of the sliders. This interpolation can be done in real time, allowing for interactive operation whereby the user can adjust a slider in region 904 and view the effect in regions 906 and/or 908.

It should be understood that GUI screen 900 is illustrative. Other types of controls can be substituted, and the layout and content of various regions can be modified as desired. The selection of treatment objectives will depend on the particular goals of radiation treatment in a given case. In some embodiments, GUI screen 900 and the supporting interpolation processes can leverage existing techniques that have been used in the context of optimizing IMRT treatment plans.

Referring again to FIG. 7, operation and updating of the GUI (block 706) can continue until, at block 708, the user indicates that a satisfactory outcome (e.g., a satisfactory dose distribution) has been produced. For instance, once a user interacting with GUI screen 900 of FIG. 9 has navigated to a combination of slider settings that provides a satisfactory dose distribution, the user may click or select "OK" button 912. "Satisfactory" in this context should be understood as meaning that the user is satisfied that: (1) the dose distribution interpolated using the current slider settings meets the goals of treatment (e.g., killing tumor cells while avoiding or limiting harm to healthy tissues); and/or (2) that further adjustment of the slider settings is not likely to lead to additional improvement.

At block 710, process 700 can generate a deliverable treatment plan based on the satisfactory outcome by the user. In the context of VMAT plans (unlike IMRT plans), it is generally not helpful to interpolate the machine parameters of different plans. Accordingly, other processes can be used to generate a deliverable plan.

Figure 10:
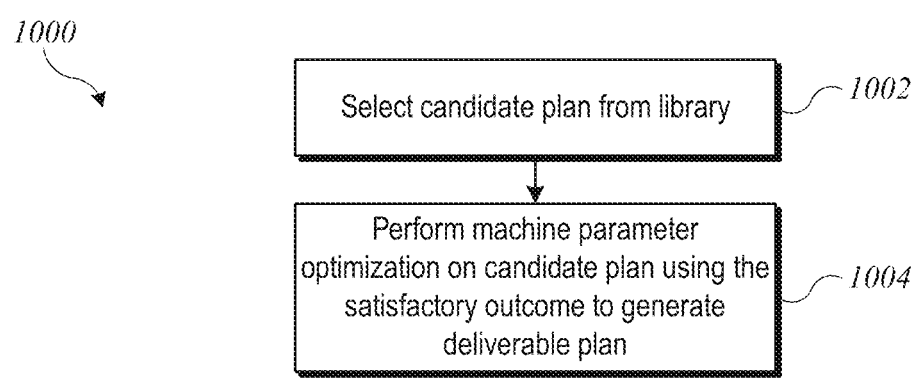
FIG. 10 shows an example of a process for generating a final deliverable VMAT treatment plan according to an embodiment of the present invention.

FIG. 10 shows an example of a process 1000 for generating a deliverable treatment plan according to an embodiment of the present invention. Process 1000 can be executed, e.g., at block 710 of process 700, at which point the user has identified a satisfactory outcome (e.g., a dose distribution) that corresponds to the current slider settings. At block 1002, process 1000 can select a "candidate" plan from the library of alternative plans. In some embodiments, the candidate plan is selected as the single alternative plan in the library whose associated dose distribution is closest to the desired dose distribution, where closeness may be measured according to the user-assigned weights (which can be derived from the slider settings). In other embodiments, other techniques can be used to select the candidate plan, such as interpolating between multiple plans that each have an associated dose distribution that is within some threshold of closeness to the desired dose distribution. At block 1004, process 1000 can perform an machine parameter adjustment optimization on the candidate plan, e.g., by continuing optimization using the (user-identified) satisfactory outcome to define the set of treatment objectives. The result of this optimization can be used as the final deliverable plan.

Once the deliverable plan has been generated at block 710, process 700 can end. Thereafter, the deliverable plan can be used to control operation of radiation treatment system 100 (or radiation treatment system 500) to perform a VMAT treatment on the patient. For instance, in embodiments where process 700 is implemented in control circuitry 560, control circuitry 560 can be instructed by the user to perform the VMAT treatment in accordance with the deliverable plan. In embodiments where process 700 is implemented on a different computer system, the deliverable plan can be represented in a computer-readable format (e.g., a configuration file conforming to a particular syntax) and delivered to control circuitry 560 using any available file-transfer mechanism (e.g., network transfer, removable storage medium). Control circuitry 560 can read and execute the deliverable plan.

In some embodiments, the outcome selected by the user may not be the best achievable outcome. Accordingly, it may be desirable to support further optimization. For example, once a deliverable plan has been generated at block 710 of process 700, this plan may be used as a seed plan for a new round of optimization by iteratively executing process 700.

Figure 11:
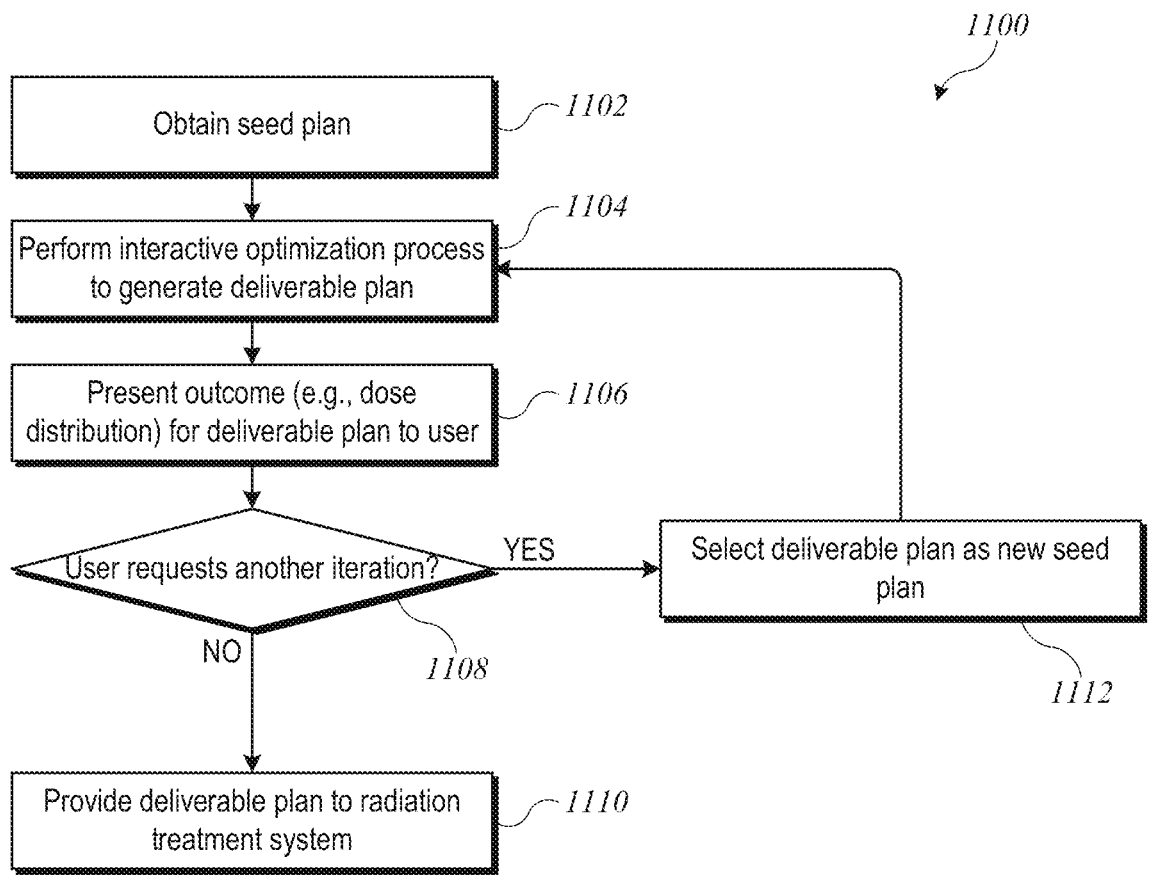
FIG. 11 shows a flow diagram of a process for iterative optimization of a VMAT treatment plan according to an embodiment of the present invention.

FIG. 11 shows a flow diagram of a process 1100 for iterative optimization according to an embodiment of the present invention. Process 1100 can be performed in a computer system, e.g., using control circuitry 560 of radiation treatment system 500 (FIG. 5) or another computer system.

At block 1102, a seed plan is obtained. This can be similar to block 702 of process 700.

At block 1104, an interactive optimization process is performed to generate a deliverable plan. This can be implemented, e.g., using blocks 704-710 of process 700.

At block 1106, dose distribution information for the deliverable plan can be presented to the user, e.g., in a GUI screen somewhat similar to GUI screen 900 of FIG. 9. For example, a dose distribution for the deliverable plan generated at block 710 of process 700 can be computed using modeling algorithms and displayed using a DVH view, dose matrix view, or the like.

At block 1108, process 1100 can determine whether the user requests another iteration or accepts the deliverable plan. For instance, the GUI screen presented to the user at block 1106 may include a prompt to the user to indicate whether to accept the deliverable plan or continue to explore the treatment space. If the user accepts the deliverable plan, then at block 1110, the deliverable plan can be provided, e.g., to control circuitry 560, which can use the deliverable plan to perform a VMAT treatment. If, at block 1108, the user chooses to continue to explore the treatment space, then at block 1112, the deliverable plan can be selected as a new seed plan, and process 1100 can return to block 1104 to perform another interactive optimization process, which includes generating additional alternative plans based on the new seed plan. In some embodiments, these additional alternative plans can be added to the library of alternative plans created during previous iteration(s) of block 1104, rather than replacing the library, thereby gradually expanding the amount of information available.

Process 1100 can be repeated any number of times. It is contemplated that the user may need to wait for a short period of time while new alternative plans are generated and possibly when the final deliverable plan is being generated. However, at each stage, interactive navigation of the treatment space can be performed as described above.

It will be appreciated that the various processes described herein are illustrative and that variations and modifications are possible. Except where internal logic requires a particular order, operations or blocks described sequentially may be executed in parallel, order of operations may be varied, and operations described in connection with different blocks can be combined. Further, it is not necessary that every operation described herein be performed in every embodiment of the invention; some operations can be omitted, and other operations not specifically described herein may be added.

Figure 12:
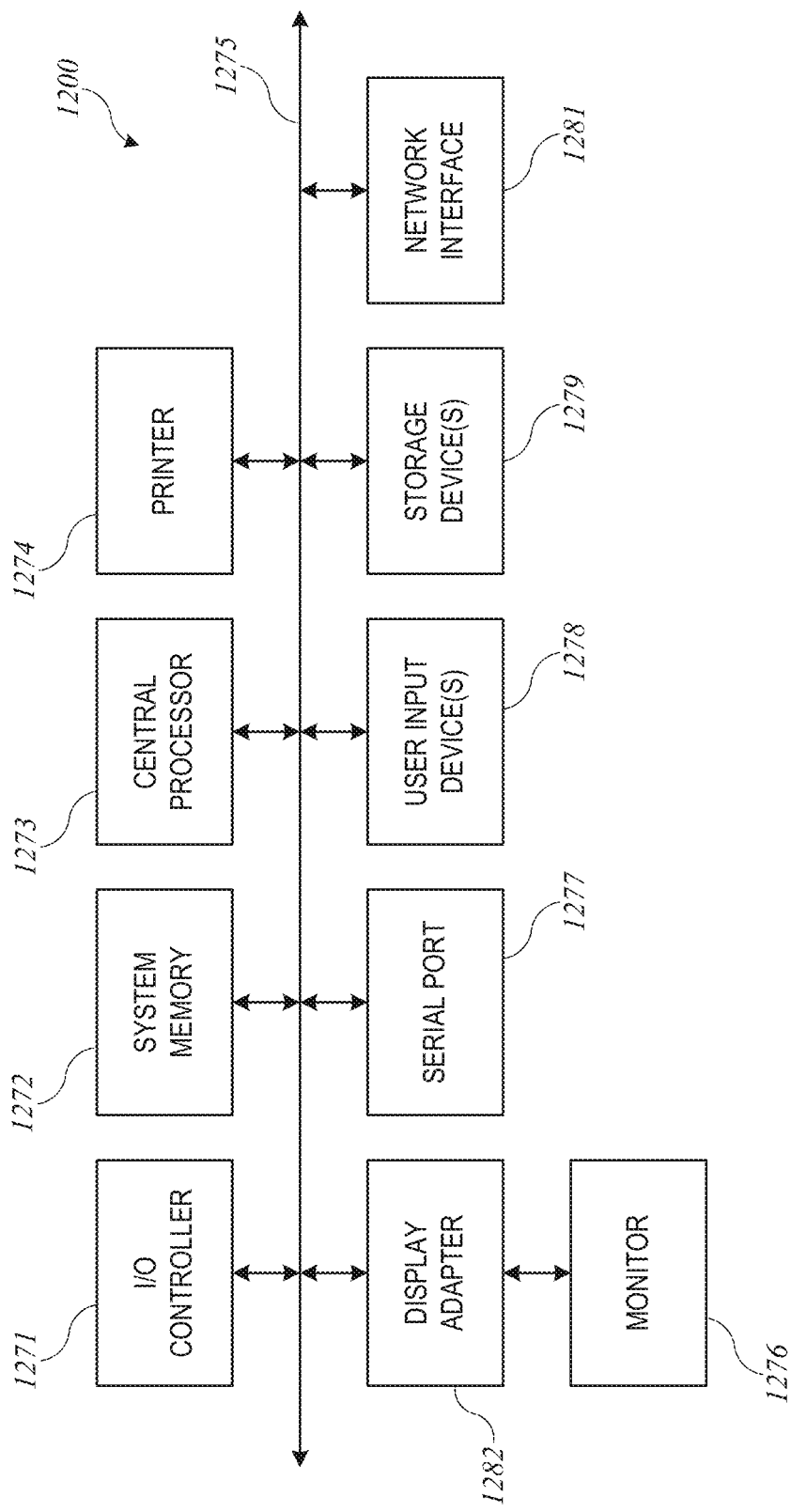
FIG. 12 shows a simplified block diagram of a computer system suitable for use in some embodiments of the present invention.

Processes described herein can be implemented in computer systems of various designs. FIG. 12 shows a simplified block diagram of a computer system 1200 suitable for use in some embodiments of the present invention. Computer system 1200 includes a number of different subsystems interconnected via a system bus 1275. The core subsystems include an input/output (I/O) controller 1271, a system memory 1272 (e.g., DRAM, SRAM, PROM, and/or other computer-readable media), and a central processor 1273. Central processor 1273, which can be implemented using one or more programmable integrated circuits (including single-core and/or multi-core microprocessors) controls operations of computer system 1200 by executing program code that can be stored (at least temporarily) in system memory 1272. Accordingly, central processor 1273 can communicate with each subsystem and can control the execution of instructions from system memory 1272 or storage device(s) 1279, as well as the exchange of information between subsystems. Similarly, any of the data mentioned herein can be delivered from one component to another component and can be output to (or input from) the user. In some embodiments, central processor 1273 may be coupled to one or more coprocessors, such as one or more graphics processing units (not shown) that are designed for high-throughput parallel processing.

I/O controller 1271 allows other components to be communicatively coupled to central processor 1273, and central processor 1273 can receive input from other components and/or send output to other components via I/O controller 1271. Accordingly, additional subsystems such as printer 1274; user input device(s) 1278 (e.g., keyboard, mouse, etc.); storage device(s) 1279 (e.g., various computer-readable media such as hard disk drives or other fixed storage devices, removable disks, removable solid-state memory devices such as USB thumb drives, etc.); monitor 1276, which is coupled to display adapter 1282; and the like may be communicably coupled to central processor 1273. Peripherals and I/O devices, which couple to I/O controller 1271, can be connected to the computer system using various interconnect standards known in the art, such as serial port 1277. Wireless local-area connectivity (e.g., via Bluetooth or Wi-Fi or the like) may also be supported.

In some embodiments, network interface 1281 may be provided to enable communication between computer system 1200 and other computer systems, e.g., via Ethernet, Wi-Fi, or the like. Network interface 1281 may support connection to a local area network and/or to a wide-area network such as the internet. Thus, for example, process 700 and/or process 1100 can be implemented in one instance of computer system 1200, which can communicate final deliverable plans to another instance of computer system 1200 local to radiation treatment system 100 (e.g., including control circuitry 560).

In some embodiments, computer system 1200 is implemented as a single computer apparatus with some or all of the subsystems described above. In some embodiments, a single instance of computer system 1200 can include multiple instances of the same components or subsystems, e.g., connected together by an internal interface. In some embodiments, two or more instances of computer system 1200 (which can be configured alike or differently as desired) can communicate over a network. In such embodiments, one instance can be considered a client and another instance a server.

It should be understood that embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a single integrated chip, or multiple microprocessors on a single circuit board or otherwise networked together to operate in a coordinated manner. Based on the disclosure and teachings provided herein, a person of ordinary skill in the art will know and appreciate other ways and/or methods to implement embodiments of the present invention using hardware and a combination of hardware and/or software.

While the invention has been described with reference to specific embodiments, those skilled in the art with access to the present disclosure will recognize that variations and modifications are possible. For example, due to currently-existing limitations of beam generation technology, VMAT treatment is currently performed using only electromagnetic radiation (energetic photons such as x-rays or gamma rays). It is contemplated that, given suitable beam generators, VMAT treatment may in the future be performed with other types of radiation (e.g., electron beams, proton beams, or other heavy ion beams), and systems and methods of the kind described herein may be used to optimize treatment plans for those types of radiation as well.

As another example, the treatment objectives described herein are generally directed toward the dose distribution for the radiation. In some cases, objectives not directly related to dose distribution may also be of interest in treatment planning. For example, where radiation is being delivered to a target volume in or near the lungs, it is usually advisable to have the patient hold her breath for the beam-on time (i.e., the duration of a continuous radiation exposure, such as the time required for gantry 20 to traverse VMAT arc 604). Breath holding can minimize motion of the lungs or neighboring tissues, allowing radiation to be more reliably delivered to the intended target. Long breath-hold times are not always possible for a patient. Accordingly, in some embodiments of treatment planning processes as described herein, one or more additional treatment objectives can be defined based on limiting the beam-on time of a VMAT treatment (e.g., traversal of a given arc) to a reasonable breath-hold time, and a user-operable control for each such treatment objective can be provided. In some embodiments, the interactive GUI screen may provide information on the beam-on time, which can be interpolated from the beam-on times of the alternative plans in the library. Other treatment objectives related to treatment time or other goals may also be defined, and interactive optimization of such objectives may be supported using a GUI similar to the examples described herein.

In some embodiments described above, a VMAT treatment consists of a single arc traversed by the beam source. In clinical practice, a radiation therapy session may include several VMAT treatments and may also include one or more IMRT treatments together with one or more VMAT treatments. The processes described herein can be used to plan individual VMAT treatments, and other processes can be used to plan a session including multiple VMAT and/or IMRT treatments.

Various features described herein, e.g., methods, apparatus, computer-readable media and the like, can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Any of the software-implemented components or functions described in this application may be realized in the form of software code to be executed by a processor; such code may be created using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may also be a combination of multiple such media.

Such programs may also be encoded and transmitted using carrier signals adapted for transmission via wired, optical, and/or wireless networks conforming to a variety of protocols, including the Internet. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network.

Any of the methods described herein may be totally or partially performed with a computer system including one or more processors, which can be configured to perform the steps. Thus, embodiments can be directed to computer systems configured to perform the steps of any of the methods described herein, potentially with different components performing different steps or different groups of steps.

Thus, while the invention has been described with reference to specific embodiments, it is to be understood that the invention is defined by the following claims.

What is claimed is:

1. A computer-implemented method for generating a volumetric modulated arc therapy (VMAT) treatment plan for providing radiation therapy to a patient, the method comprising:
    providing a library including a plurality of alternative plans for a VMAT treatment, the plurality of alternative plans representing a treatment space defined by a plurality of treatment objectives, each alternative plan having an associated outcome for the plurality of treatment objectives, wherein providing the library includes:
        receiving, from a user, an initial seed plan and information indicating the plurality of treatment objectives;
        creating, from the initial seed plan, a plurality of optimized plans, wherein each optimized plan is optimized with respect to a different one of the treatment objectives by adjusting machine parameters of the initial seed plan; and
        including each of the optimized plans as one of the alternative plans in the library;
    generating a graphical user interface having a plurality of navigation controls operable by a user to navigate within the treatment space, the graphical user interface presenting a dynamically updated current outcome based in part on the outcomes associated with the alternative plans in the library and in part on current settings of the navigation controls;
    receiving user input via the graphical user interface, the user input indicating that the current outcome is a satisfactory outcome;
    selecting, based on the satisfactory outcome, a candidate plan from the plurality of alternative plans in the library; and
    performing a machine parameter optimization on the candidate plan, using the satisfactory outcome, to generate a deliverable plan.

2. The method of claim 1 wherein each optimized plan is Pareto-optimal with respect to the treatment objectives.

3. The method of claim 1 wherein the initial seed plan includes a set of control points and wherein adjusting the machine parameters of the initial seed plan includes modifying one or more of the control points in the set of control points.

4. The method of claim 3 wherein each control point specifies a spatial location for a beam source that produces a beam of radiation and associates with the spatial location one or more of:
    a collimator setting for the beam source;
    a dose rate for the beam; or
    a speed of motion of the beam source.

5. The method of claim 1 wherein the candidate plan includes a set of control points and wherein performing the machine parameter optimization on the candidate plan includes modifying one or more of the control points in the set of control points.

6. The method of claim 5 wherein each control point specifies a spatial location for a beam source that produces a beam of radiation and associates with the spatial location one or more of:
    a collimator setting for the beam source;
    a dose rate for the beam; or
    a speed of motion of the beam source.

7. The method of claim 1 wherein the plurality of treatment objectives includes a first treatment objective corresponding to a radiation dose to be delivered to a target volume and a second treatment objective corresponding to a radiation dose to be delivered to an organ at risk that is located near the target volume.

8. The method of claim 7 wherein the target volume corresponds to a location of a tumor.

9. The method of claim 7 wherein the plurality of treatment objectives further includes a third treatment objective corresponding to a beam-on time of a VMAT treatment.

10. The method of claim 1 wherein the navigation controls of the graphical user interface are operable to indicate a relative importance of each of the treatment objectives.

11. The method of claim 1 wherein the dynamically updated current outcome presented in the graphical user interface is generated by an interpolation from the associated outcomes of at least some of the alternative plans.

12. The method of claim 11 wherein the interpolation is based at least in part on the current settings of the navigation controls.

13. The method of claim 1 wherein the candidate plan is the one of the alternative plans in the library that matches the satisfactory outcome more closely than any other of the alternative plans in the library.

14. The method of claim 1 further comprising:
operating a radiation treatment system in accordance with the deliverable plan to perform a VMAT treatment on the patient.

15. A computer-implemented method for generating a volumetric modulated arc therapy (VMAT) treatment plan for providing radiation therapy to a patient, the method comprising:
obtaining, from a user, an initial seed plan and a set of treatment objectives;
performing a first iteration of an interactive optimization process using the initial seed plan, wherein the iteration of the interactive optimization process results in generation of a deliverable plan;
receiving input from the user indicating whether the deliverable plan is accepted;
in the event that the deliverable plan is accepted, providing the deliverable plan for use in a radiation treatment system; and
in the event that the deliverable plan is not accepted, selecting the deliverable plan as a new seed plan and performing another iteration of the interactive optimization process using the new seed plan,
wherein each iteration of the interactive optimization process includes:
providing a library including a plurality of alternative plans for a VMAT treatment, the plurality of alternative plans representing a treatment space defined by a plurality of treatment objectives, each alternative plan having an associated outcome for the plurality of treatment objectives, at least some of the alternative plans being generated based on the seed plan of the current iteration, wherein providing the library includes creating, from the seed plan of the current iteration, a plurality of optimized plans, each optimized plan being optimized with respect to a different one of the treatment objectives, and including each of the optimized plans as one of the alternative plans in the library;
generating a graphical user interface having a plurality of navigation controls operable by a user to navigate within the treatment space, the graphical user interface presenting a dynamically updated current outcome based in part on the outcomes associated with the alternative plans in the library and in part on current settings of the navigation controls;
receiving user input via the graphical user interface, the user input indicating that the current outcome is a satisfactory outcome;
selecting, based on the satisfactory outcome, a candidate plan from the plurality of alternative plans in the library; and
performing a machine parameter optimization on the candidate plan, using the satisfactory outcome, to generate the deliverable plan.

16. The method of claim 15 wherein each optimized plan is Pareto-optimal with respect to the treatment objectives.

17. The method of claim 15 wherein the seed plan includes a set of control points and wherein adjusting the machine parameters of the seed plan includes modifying one or more of the control points in the set of control points.

18. The method of claim 17 wherein each control point specifies a spatial location for a beam source that produces a beam of radiation and associates with the spatial location one or more of:
a collimator setting for the beam source;
a dose rate for the beam; or
a speed of motion of the beam source.

19. The method of claim 15 wherein, for each iteration of the interactive optimization process, the candidate plan includes a set of control points and wherein performing the machine parameter optimization on the candidate plan includes modifying one or more of the control points in the set of control points.

20. The method of claim 19 wherein each control point specifies a spatial location for a beam source that produces a beam of radiation and associates with the spatial location one or more of:
a collimator setting for the beam source;
a dose rate for the beam; or
a speed of motion of the beam source.

21. The method of claim 15 wherein the set of treatment objectives includes a first treatment objective corresponding to a radiation dose to be delivered to a target volume and a second treatment objective corresponding to a radiation dose to be delivered to an organ at risk that is located near the target volume.

22. The method of claim 21 wherein the target volume corresponds to a location of a tumor.

23. The method of claim 21 wherein the set of treatment objectives further includes a third treatment objective corresponding to a duration of a VMAT treatment.

24. The method of claim 15 wherein the navigation controls of the graphical user interface are operable to indicate a relative importance of each of the treatment objectives.

25. The method of claim 15 wherein the dynamically updated current outcome presented in the graphical user interface is generated by an interpolation from the associated outcomes of at least some of the alternative plans.

26. The method of claim 25 wherein the interpolation is based at least in part on the current settings of the navigation controls.

27. The method of claim 15 wherein the candidate plan is the one of the alternative plans in the library that matches the satisfactory outcome more closely than any other of the alternative plans in the library.

28. The method of claim 15 further comprising:
in the event that the deliverable plan is accepted, operating the radiation treatment system in accordance with the deliverable plan to perform a VMAT treatment on the patient.

* * * * *